(12) United States Patent
Nguyen

(10) Patent No.: US 10,709,902 B2
(45) Date of Patent: Jul. 14, 2020

(54) TANDEM WITH CAMERA SYSTEM AND METHOD

(71) Applicant: Dung B. Nguyen, Mansfield, OH (US)

(72) Inventor: Dung B. Nguyen, Mansfield, OH (US)

(*) Notice: Subject to any disclaimer, the term of this patent is extended or adjusted under 35 U.S.C. 154(b) by 244 days.

(21) Appl. No.: 15/718,118

(22) Filed: Sep. 28, 2017

(65) Prior Publication Data

US 2018/0085601 A1 Mar. 29, 2018

Related U.S. Application Data

(60) Provisional application No. 62/400,896, filed on Sep. 28, 2016.

(51) Int. Cl.
  *A61N 5/10* (2006.01)
(52) U.S. Cl.
  CPC ......... *A61N 5/1039* (2013.01); *A61N 5/1014* (2013.01); *A61N 5/1016* (2013.01); *A61N 5/1049* (2013.01); *A61N 2005/1059* (2013.01)
(58) Field of Classification Search
  CPC ...... A61N 5/1001–1016; A61N 5/1039; A61N 2005/1059
  See application file for complete search history.

(56) References Cited

U.S. PATENT DOCUMENTS

| | | |
|---|---|---|
| 6,311,084 B1 | 10/2001 | Cormack et al. |
| 6,360,116 B1 | 3/2002 | Jackson, Jr. et al. |
| 6,549,802 B2 | 4/2003 | Thornton |
| 7,412,029 B2 | 8/2008 | Myles |
| 7,817,836 B2 | 10/2010 | Chao et al. |
| 8,295,910 B1 | 10/2012 | Weisenberger et al. |
| 2005/0027196 A1 | 2/2005 | Fitzgerald |
| 2010/0298640 A1 | 11/2010 | Oneda et al. |
| 2011/0257515 A1* | 10/2011 | Atalar ............... A61B 5/055 600/422 |
| 2013/0109908 A1* | 5/2013 | Rahimian ............ A61N 5/1016 600/6 |
| 2014/0121245 A1 | 5/2014 | Konakanchi et al. |
| 2014/0121445 A1 | 5/2014 | Fontenot et al. |
| 2014/0275713 A1 | 9/2014 | Bask et al. |
| 2015/0230696 A1* | 8/2015 | Tuch ................. A61B 5/0077 600/431 |
| 2015/0272430 A1 | 10/2015 | Oishi et al. |
| 2016/0045098 A1 | 2/2016 | Tsubouchi |

(Continued)

FOREIGN PATENT DOCUMENTS

| | | |
|---|---|---|
| WO | 2002082820 A1 | 10/2002 |
| WO | 2014021513 A1 | 2/2014 |

*Primary Examiner* — Thaddeus B Cox
(74) *Attorney, Agent, or Firm* — Jacob M. Ward; Ward Law Office LLC

(57) ABSTRACT

A tandem applicator assembly for brachytherapy that includes a tandem and a camera system. The tandem has a tubular main body with a trail end and a lead end. A transparent cap is affixed to the lead end. The camera system is removably received by the tandem through the trail end of the tubular main body. The camera system is disposed inside of the transparent cap. The camera system includes at least one digital camera configured to acquire color images from a patient through the transparent cap. The tandem applicator assembly may be used with a treatment planning system and method for customizing a treatment plan for a patient undergoing brachytherapy.

14 Claims, 8 Drawing Sheets

(56) References Cited

U.S. PATENT DOCUMENTS

| | | |
|---|---|---|
| 2016/0193480 A1 | 7/2016 | Ribbing et al. |
| 2016/0235340 A1* | 8/2016 | Sidar ...................... A61B 5/065 |
| 2018/0092700 A1* | 4/2018 | Itkowitz ................. A61B 34/25 |

* cited by examiner

TANDEM WITH CAMERA SYSTEM AND METHOD

CROSS-REFERENCE TO RELATED APPLICATIONS

This application claims the benefit of U.S. Provisional Application No. 62/400,896, filed on Sep. 28, 2016. The entire disclosure of the above application is hereby incorporated herein by reference.

FIELD

The present disclosure relates to a system and method for treatment of cancer and, more particularly, to a brachytherapy system and method for visualization of the tissue to be treated in real-time or near real-time.

BACKGROUND

Cancers involving the uterus and/or the cervix may be optimally managed with definitive radiotherapy or radiochemotherapy. Since cancer often affects organs and other essential structures, it is important for such radiation treatments to be tightly focused on tumors to minimize serious side effects. This ensures the maximum radiation dose is given to cancerous tissues, while minimizing exposure to the surrounding healthy tissue.

One common radiation treatment strategy is brachytherapy, typically by either a low dose rate (LDR) or a high dose rate (HDR) with radioactive sources. Brachytherapy typically requires the placement of a tandem applicator into the uterine cavity through the cervical os. This is often done "blindly," by advancing the tandem until the brachytherapist senses slight resistance to indicate that the tandem tip has approximated the uterine fundus. The risk of uterine perforation using this technique is undesirable, and may adversely affect patient outcomes.

Furthermore, once the positioning of the tandem applicator is completed, it is important for the brachytherapist to quickly develop a plan for insertion of the radioactive sources at desired dwell positions, and for desired times, by a brachytherapy machine, in order to provide more efficient treatment, minimize discomfort for the patient, and minimize the time clinically trained staff will need to spend caring for the patient. However, known methods for optimization of dwell positions and dwell times for brachytherapy are cumbersome and time consuming.

One known technique for 'real-time' verification of tandem position is intraoperative ultrasonography. However, this technique requires specialized and expensive equipment, as well as a significant amount of training and expertise to be effective.

Another known strategy is described in U.S. Published Patent Application No. 2014/0121245 to Fontenot et al. A brachytherapy application device is described in Fontenot et al, which includes a tandem having a transparent region at its front end, and which is coupled with a fiber-optic illumination means and endoscope. The Fontenot et al. tandem assembly allows the user to guide the tandem into the uterus of a patient in a safer, more reproducible manner with the reduction in occurrence of uterine perforation during tandem advancement and placement. However, the subsequent insertion of radioactive sources into the tandem applicator for each patient can still be undesirably time-consuming and requires significant training.

There is a continuing need for a system and method that permits a visualization of the brachytherapy procedure, so as to avoid blind insertions and the risks of perforations. Desirably, the system and method further permits an efficient development of a treatment plan personalized to the patient based on a real-time or near real-time imaging during the brachytherapy procedure.

SUMMARY

In concordance with the instant disclosure, a system and method that permits a visualization of the brachytherapy procedure, so as to avoid blind insertions and the risks of perforations, and which further permits an efficient development of a treatment plan personalized to the patient based on a real-time or near real-time imaging during the brachytherapy procedure, is surprisingly discovered.

In one embodiment, a tandem applicator assembly for brachytherapy includes a tandem and a camera system. The tandem has a tubular main body with a trail end and a lead end. A transparent cap is affixed to the lead end. The camera system is removably received by the tandem through the trail end of the tubular main body. The camera system is disposed inside of the transparent cap. The camera system includes at least one digital camera configured to acquire color images from a body cavity of a patient through the transparent cap.

In certain examples, the transparent cap may be formed from glass. The transparent cap may also be removably attached to the lead end of the tandem, for example, through the use of a threaded exterior of the cap cooperating with a threaded interior of the tandem. Other means for attaching the transparent cap may also be used, as desired.

The camera system may have a main body including a camera portion with at least one protective lens. The at least one digital camera is disposed inside of the main body. The at least one digital camera is configured to acquire the color images of the patient through both the at least one lens and the transparent cap. The main body may further be provided with a light unit, such as an LED light, that is configured to illuminate the body cavity of the patient and to facilitate the acquisition of the color digital images.

The main body of the camera system may further include a processor and a memory, which are in communication with the at least one camera. The processor may be configured to pre-process the color images of the body cavity of the patient, for example, to form a composite image (e.g., a three-dimensional model) of the body cavity that may be used for treatment planning purposes. The memory may be configured to store both the color images and the composite image, as desired.

The main body may further have a transmitter in communication with the processor and the memory. The transmitter is configured to generate at least one of a wired signal and a wireless signal with image data, for example, relating to at least one of the color images and the composite image. The transmitter may further be in communication by wire through the insertion and removal line with a computer having a screen on which the color images or the composite image are generated. Where the transmitter is configured to wirelessly transfer the image data, e.g., by a wireless signal such as Bluetooth®, a portion of the transmitter may also abut a surface of the tandem, which causes the entire or part of the tubular main body of the tandem to function as an antenna of the transmitter for transmission for the wireless signal. In this case, the transmitter may be in communication wirelessly with a handheld mobile device, such as a smart phone, having a screen on which the color images or the composite image are generated using an associated "app" or computer software.

In another embodiment, a brachytherapy method involves using the tandem applicator assembly with the camera system. The tandem applicator assembly is inserted into a body cavity of the patient while acquiring the color images in real-time or near real-time. The color images are reviewed by the user in order to confirm a desired positioning of the tandem applicator assembly within the body cavity of the patient. The camera system is then removed from the tandem. A radioactive source is then inserted and moved through the trail end of the tubular main body to administer radiation to the patient according to a treatment plan.

In various examples, the camera system may be in communication with a treatment planning system. The treatment planning system may include a computer with a processor and a memory defined by a non-transitory, tangible computer readable storage medium. The memory has processor-readable instructions embodied thereon, and by which the processor is configured to generate an image on a computer screen of the tandem and an editable dose-volume histogram associated with the treatment plan. A user may be permitted, by a user interface of the computer of the treatment planning system, to add at least one dwell position to the image of the tandem, and to adjust at least one dwell time associated with the at least one dwell position. The at least one dwell position may be identified by a symbol generated by the treatment planning system on the dose-volume histogram, for example. The symbol may change in at least one of shape, color, and size depending on a magnitude of the at least one dwell time associated with the at a least one dwell position and the symbol. The treatment planning system may be further configured to plot curves on the dose-volume histogram as the user performs maneuvers according to the at least one dwell position and the at least one dwell time. A user may also be permitted, by a user interface of the computer of the treatment planning system, to view on the computer screen the color images, which may be translucent, of the body cavity and organs of the patient, to facilitate a creation of the treatment plan.

In a further embodiment, a computer-implemented system for brachytherapy includes the tandem and the treatment planning system. The treatment planning system includes a computer with a processor and a memory defined by a non-transitory, tangible computer readable storage medium. The memory has processor-readable instructions embodied thereon, and which are configured to generate by the processor an image of the tandem and an editable dose-volume histogram associated with the treatment plan on a computer screen. A user is permitted, by a user interface of the computer of the treatment planning system, to add at least one dwell position to the image of the tandem, and to adjust at least one dwell time associated with the at least one dwell position. The at least one dwell position may be identified by a symbol generated by the treatment planning system on the dose-volume histogram. The symbol may change in at least one of shape, color, and size depending on a magnitude of the at least one dwell time associated with the at a least one dwell position and the symbol. The treatment planning system is further configured to plot curves on the dose-volume histogram as the user performs maneuvers by identifying the at least one dwell position and the at least one dwell time.

DRAWINGS

The above, as well as other advantages of the present disclosure, will become readily apparent to those skilled in the art from the following detailed description, particularly when considered in the light of the drawings described hereafter.

DETAILED DESCRIPTION

Figure 1:
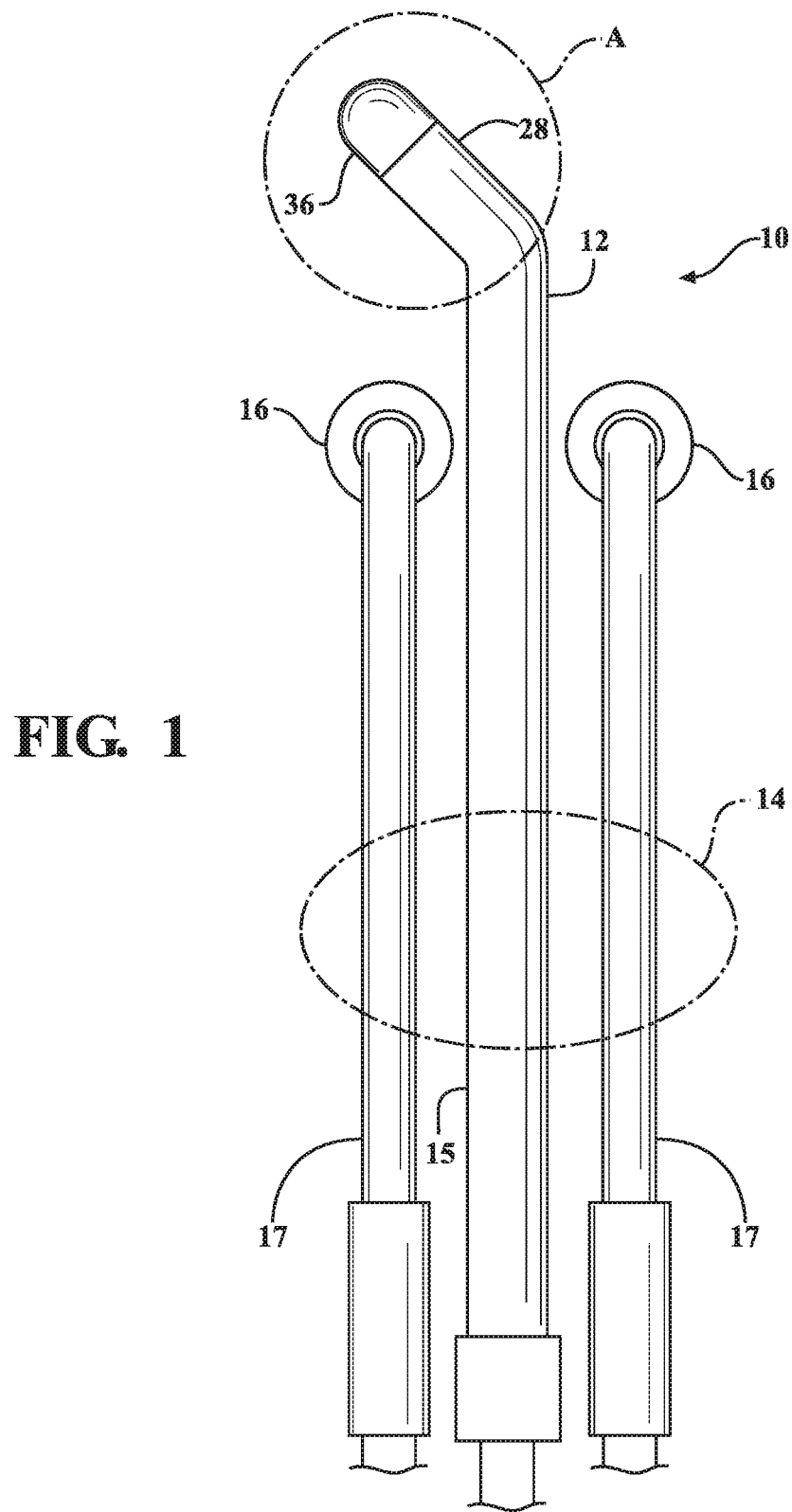
FIG. 1 is a partial side elevational view of an exemplary tandem applicator assembly according to the present disclosure, having a transparent cap and configured to be inserted into a uterus.

The following description is merely exemplary in nature and is not intended to limit the present disclosure, application, or uses. It should also be understood that throughout the drawings, corresponding reference numerals indicate like or corresponding parts and features. In respect of the methods disclosed, the steps presented are exemplary in nature, and thus, are not necessary or critical.

I. Tandem Applicator Assembly:

In FIG. 1, an exemplary tandem applicator assembly 10 according to one embodiment of the present disclosure is shown. The assembly 10 includes a tandem 12 connected to a pivot joint 14 through a tandem arm 15 and, optionally, a pair of colpostats/ovoids or ring 16 which are connected to the pivot joint 14 through a pair of ovoid or ring arms 17. In certain embodiments, the pivot joint 14 serves only to connect the tandem arm 15 to the ovoid arm 17, while in other embodiments the pivot joint 14 functions not only as a connection point, but also enables alterations of the angle between the tandem arm 15 and the ovoid arm 17.

The tandem 12 is a substantially tubular main body configured to hold one or more therapeutic radioactive source(s) (not shown), such as an iridium or cesium isotope, as non-limiting examples, during selective irradiation of a patient 18 (shown in FIG. 2), such as during a brachytherapy application. In certain embodiments, the tandem arm 15 may be adapted to allow the radioactive source(s) to be loaded through them into the tandem 12. In operation, this can be done after the tandem 12 has been positioned within the body cavity in a process termed "after-loading."

Figure 2:
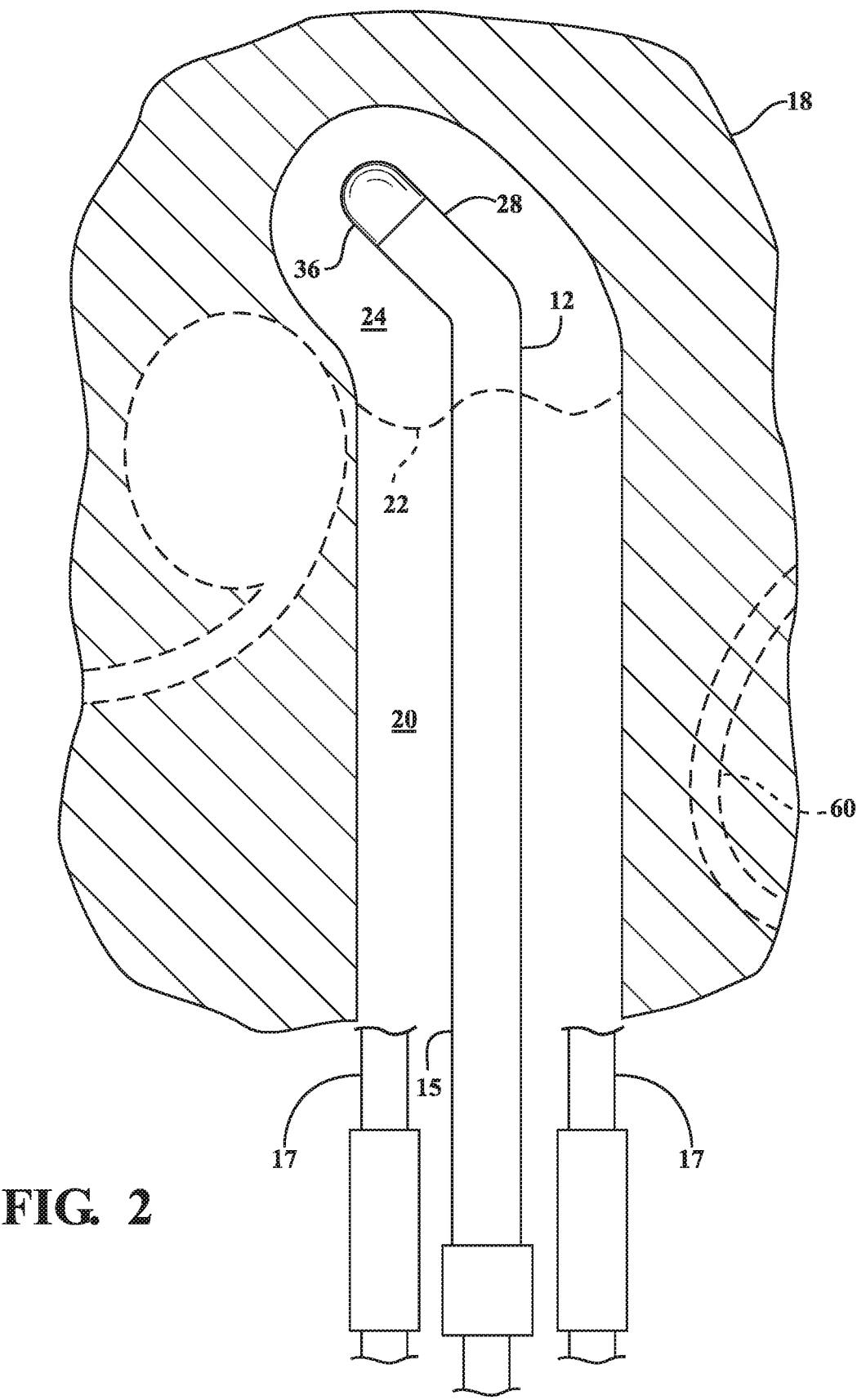
FIG. 2 is a partial side elevational view illustrating the tandem applicator assembly shown in FIG. 1, having been inserted into the uterus of a patient for brachytherapy treatment.

FIG. 2 depicts a general illustration of the positioning of the tandem applicator assembly 10 of the present disclosure during treatment of a patient 18 having cervical cancer. It should be appreciated that the tandem 12 may be used for treatment of other types of conditions or cancers, as desired.

In the case of treatment for cervical cancer, the tandem 12 is inserted though the vaginal cavity 20 and the cervix 22 into the uterus 24, for example, while the ovoids 16 may be positioned in the vaginal cavity 20 proximal to the external os of the cervix 22. Upon being positioned, the tandem applicator assembly 10 of the present disclosure may be used for an intracavitary brachytherapy treatment procedure. The radioactive sources can then be after-loaded into the tandem 12 in order to provide a generally spherical- or pear-shaped dose distribution that just surrounds a target volume, with its long axis along the tandem axis.

Prior to the loading of the radioactive source during such procedures, the tandem applicator assembly 10 is positioned in the body cavity using a real-time image feed from a camera system 26, which may be removably positioned at a lead-end 28 of the tandem 12, as will be described in further detail below with reference to FIG. 3. The lead-end 28 may be angled relative to the remainder of the tandem 12, as shown, or may be collinear with the remainder of the tandem 12, as desired.

It should be understood that using the camera system 26 in accordance with further aspects of the present disclosure desirably supplements the images from a variety of other, external (i.e., outside of the tandem 12) sources such as orthogonal X-ray films, CT scans, MR scans, and/or PET scans, to confirm the location of the tandem applicator assembly 10 in the patient 18. The camera system 26 provides supplementary images sufficient to verify that the tandem applicator assembly 10 has been positioned optimally with respect to anatomical location and the dosage of radiation that will be delivered to the targeted area.

Figure 3:
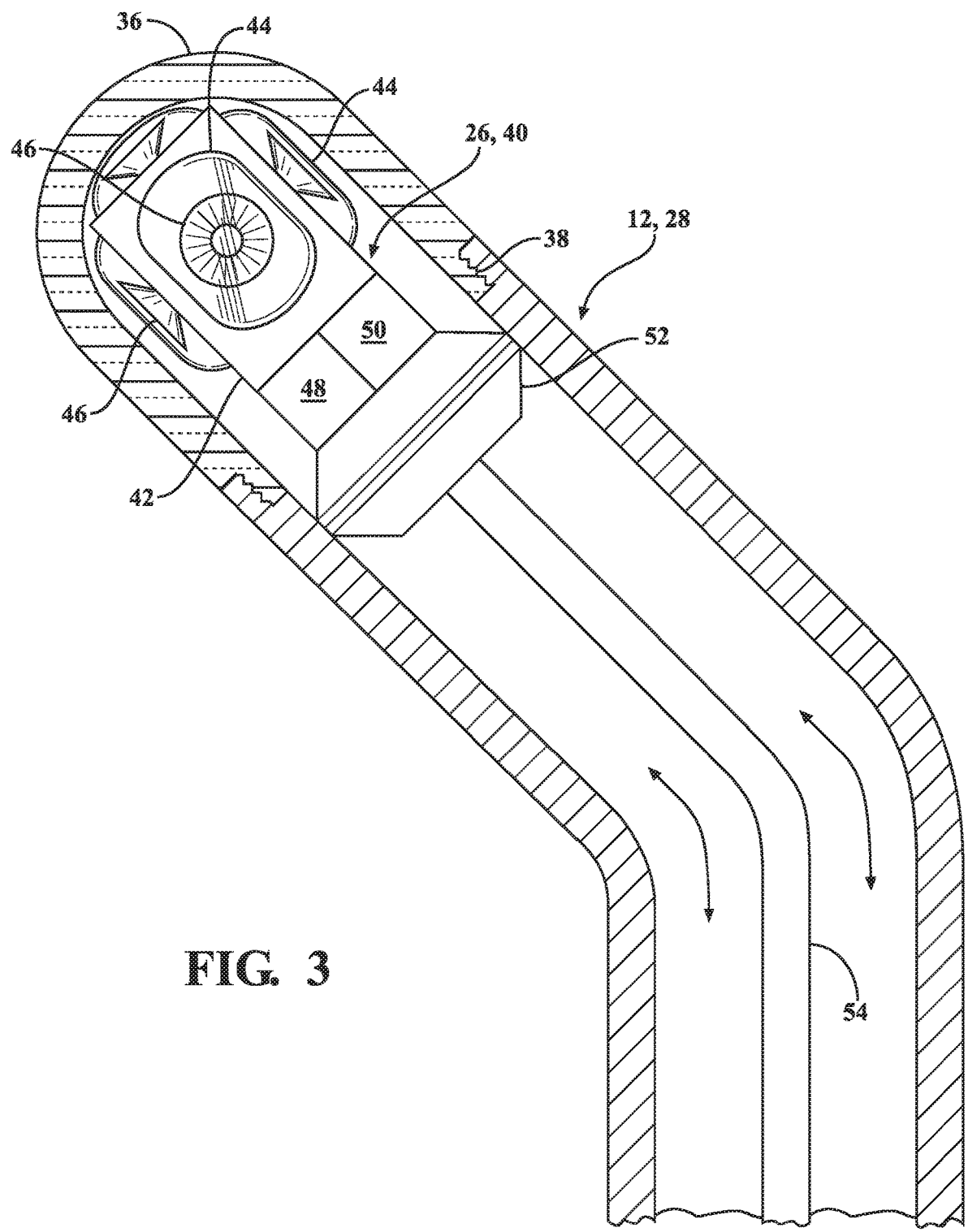
FIG. 3 is an enlarged cross-sectional view of the tandem applicator assembly taken at call-out A in FIG. 1, illustrating the camera, microprocessor, memory, and transmitter/receiver assembly removably disposed inside of the transparent cap of the tandem.
Figure 4:
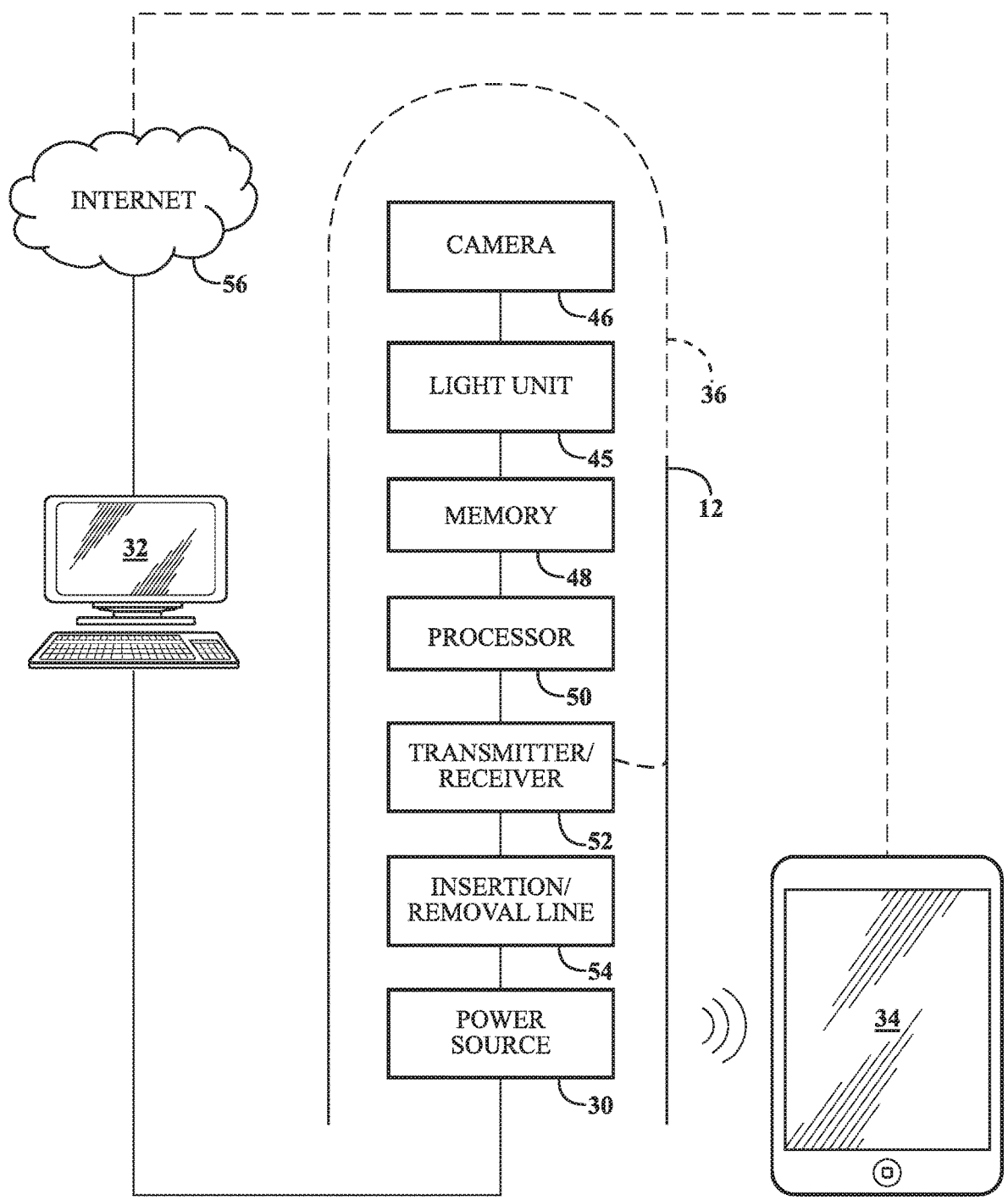
FIG. 4 is a schematic diagram of the tandem shown in FIG. 4, and further illustrating a network connection of the assembly with an external computer and mobile device.

With reference to FIGS. 3 and 4, the tandem 12 may be supported by a handle assembly (not shown), and which is further connected to a power source 30, such as a battery or a plug connection to a power grid, and an image-viewing device 32, 34, such as a personal computer 32 with a monitor, a handheld mobile device 34, or the like, as shown in FIG. 4.

In particular, the lead-end 28 of the tandem 12 is generally hollow and configured to removably receive the camera system 26. A majority of the length of the tubular main body of the tandem 12 may be fabricated from a suitably rigid material, e.g., a metal such as stainless steel or a composite material, so as to facilitate the maneuvering of the lead end 28 (i.e., the insertion portion) of the tandem 12 through an orifice into a desired interior cavity of the patient 18. Preferably, the tube forming the tandem 12 is cylindrical as shown, although it may also be formed with some other suitable geometrical cross-sectional shape, including elliptical, oblong/oval and square, as desired.

As shown in FIG. 3, the lead end 28 of tandem 12 has a transparent cap 36. The cap 36 is formed from a transparent material such as glass or plastic so as to allow the camera system 26 contained within the tandem 12 to acquire digital images of the patient 18. The cap 36 may be permanently affixed to the tandem arm 15 using an appropriate attachment means, such as an adhesive (chemical bonding) or by a mechanical attachment mechanism, such as screws as by a set of matching screw threads 38 allowing for the mating of the bottom lip of the cap 36 to the inner surface of the tandem 12.

The cap 36 may selectively house the camera system 26 therein. The camera system 26 includes a main body 40 having a camera portion 42 with at least one lens 44. The at least one lens 44 may include one or more high-quality lenses with specific indices of refraction, and being designed to provide a sharply-focused image on an imaging source (e.g., a display monitor on a computer or hand-held device) that is substantially free of visual defects such as chromatic aberrations.

The camera portion 42 may also have an illumination source 45, such as an LED light unit 45, that serves as a means for illuminating the area immediately in front of the at least one lens 44 through the transparent cap 36. The illumination source 45 thereby enhances the viewing by a user of the camera system 26. The illumination source 45 may be coupled to the camera portion 42, or housed within the main body 40 of the camera portion 42 behind one of the lenses 44, as desired. Optionally, in accordance with another embodiment of the present disclosure, the illumination source 45 may be a separate tube line running coaxial to camera system 26, rather than being housed in or attached to the main body 40 of the camera system 26.

The illumination source 45 is selected to be appropriate for the level of object illumination needed for mapping the volume to be treated. For example, and without limitation, a 10,000 lux, 1.25 W LED may provide adequate illumination, although other alternative light sources such as those providing an illumination of 70,000 lux exhibit substantially ideal illumination for gynecological applications. The assembly 10 can also include a voltage regulator coupled to the light unit 45 so as to adjust the degree of illumination, as desired.

It should also be appreciated that the illumination source 45 together with the transparent cap 36 may conduct light into the cavity in a directed manner, for example, via total internal reflection. In this manner, the illumination source 45 may provide "beams" of light directed forward from the camera system 46 to facilitate the maneuvering of the tandem 12 when inserted into the patient.

With renewed reference to FIG. 3, it should be appreciated that the camera portion 42 includes at least one digital camera 46 configured to provide color images or video in real-time or near real-time, and in accordance with select aspects is associated with a system for viewing the images as well as recording and documenting the tandem 12 placement in vivo as will be described further herein. In particular embodiments, the camera portion 42 includes more than one digital camera 46 that can be used to convey a sense of depth perception, as is often required to provide a three-dimensional observation image or model.

In a particular embodiment, the at least one digital camera 46 includes a plurality of digital cameras 46 disposed about the camera portion 42 at predetermined viewing angles. Likewise, the transparent cap 36 may be an entirely transparent dome, providing in a 360 degree view about the camera portion 42 in order to permit the acquisition of color images of the substantial entirety of the volume into which the tandem 12 is inserted.

The camera portion 42 may further include a memory 48 and a processor 50 in communication with the at least one digital camera 46. The memory 48 is a tangible, non-transitory computer-readable medium configured to receive and store image data from the at least one camera 46. The memory 48 may also contain processor-executable instructions, which the processor 50 (e.g., an integrated circuit microprocessor) may use to pre-process the image data into composite images viewable by the user as a model of the volume into which the tandem 12 has been inserted.

The camera portion 42 may further have a transmitter/receiver 52 that is in communication with the memory 48 and the processor 50, and configured to transmit signals including the image data to the at least one image-viewing device 32, 34 external to the body of the patient 18. The transmitter/receiver 52 may further be configured to receive signals from a user interface of the at least one image-viewing device 32, 34, for example, to permit the user to adjust at least one of the focus of the at least one camera 46 and an intensity of the illumination source 45, as desired.

Although the transmitter/receiver 52 is shown in FIGS. 3 and 4 provided as a single unit, it should be understood that the transmitter and receiver may be provided separately, or only the transmitter or only the receiver may be provided in communication with the memory 48 and the processor 50, within the scope of the present disclosure.

As shown in FIG. 3, a portion of the transmitter/receiver 52 may advantageously abut or contact a surface of the tandem 12. Where the tandem 12 is formed from a conductive metal or composite material, for example, the tandem 12 through contract with the transmitter/receiver 52 may function as an antenna for purpose of wireless transmission of the signals. For example, the transmitter/receiver 52 may be configure to directly transmit a wireless radio signal, such as a Bluetooth® signal, to a mobile device 34 running an application configured to receive such signals and display on a screen thereof the color images or a pre-processed model formed by composite images transmitted from the camera portion 42.

Coupled to the main body 40 of the camera system 26 is also an insertion and removal line 54. The insertion and removal line 54 includes a thin wire or cable that permits for an automated or manual insertion and removal of the camera system 26 through the hollow body of the tandem 12 to the transparent cap 36, where the camera system 26 may be used to capture images as the tandem 12 is inserted into a body cavity of the patient 18. In certain embodiments, the insertion and removal line 54 may also include at least one of a wire and a fiber optic cable that permits a non-wireless transmission of the signals to and from the transmitter/receiver 52. In this manner, the color images or the pre-processed model may be delivered to the computer 32 that is directly connected by the insertion and removal line 54 and shown on the related monitor.

It should further be appreciated that the computer 32, which in turn has a processor and non-transitory tangible memory, may be connected to a wide area network 56 such as the Internet. In this manner, the color images and pre-processed models may optionally be shared via a suitable encryption process for privacy protection through the wide area network 56 to other computers and devices, including the handheld mobile device 34 running the application for viewing the color images or pre-processed models in real-time or near real-time.

Furthermore, it should be understood that the computer 32 or the handheld mobile device 34 may alternately be configured through software or related applications to process or reconstruct the color images into the models in real-time or near real-time, thereby minimizing the need for pre-processing by the processor 50 of the camera system 26 within the tandem 12.

The acquisition of digital color images by the at least one digital camera is particularly beneficial, especially relative to known uses of endoscopes with fiber-optic illumination. The real-time or near real-time digital color imagery allows the user to detect bleeding, measure a velocity of blood flow, and to compare tumor size, texture, and coloration. Likewise, the image processing advantageously allows for the creation of a model that is usable in determining sufficient dwell positions and dwell times according to the treatment planning method that is described further herein.

In operation, the tandem applicator assembly 10 of the present disclosure, having the transparent or glass cap 36 and the camera system 40 shown in FIGS. 1-4, allows for the small digital camera or cameras 46 to be inserted into the tandem 12 to the transparent cap 36 so that the insertion into the hollow body cavity, such as the uterus, can be visualized in real-time. Once the tandem 12 is inserted, the camera(s) 46 can be removed. The tandem/ovoid/ring then can be used per usual brachytherapy practices, i.e., to house radioactive sources introduced into its length to treat cancer. It should be appreciated that the same dwell positions and dwell times may be used for the ring, and dwell times may be calculated for the ovoids.

II. Treatment Planning System and Method of Use:

The tandem applicator assembly 10 described hereinabove, in addition to permitting image-guided tandem 12 placement, may further be used in a treatment planning system and method for dose planning, i.e., a determination of how long must a radioactive source stay at a given location in the tandem 12 so that the dose is maximally delivered to the cancer while minimizing the dose to the normal organs (such as bladder 58 in front and rectum 60 behind, as shown in FIG. 2). As established hereinabove, known software requires numerous numerical adjustments that are non-intuitive, i.e., provides no visual feedback in real-time, and therefore is inefficient and requires significant training and experience.

The apparatus described herein can be used to deliver radiation that is useful in treating any appropriate body tissue in a subject affected by a proliferative condition. Proliferative conditions include tumors, cancers, or other manifestations of abnormal cellular division. For example, and without limitation, the apparatus of the present disclosure may be used, alone or in combination, to treat adenocarcinomas, carcinomas, leukemias, lymphomas, myelomas, sarcomas, and mixed-type cancers in a subject so affected. Gynecologic cancers such as cervical cancer, endometrial cancer, uterine cancer, ovarian cancer, and vaginal cancer may particularly benefit from visualization and treatment with the apparatus described herein due their conformable and spacing features. Radiation of the vaginal cuff (e.g., after hysterectomy) for endometrial cancer with or without adjuvant pelvic external beam radiation, may also be performed with the apparatus described herein, with appropriate modification.

Radiation therapy for proliferative conditions is generally administered over a period of time in partial doses, or fractions, the sum of which comprises a total prescribed dose. For example, about two to about four fractions may be used for vaginal cuff brachytherapy with a total dose of about 10 Gy to about 30 Gy to the target tissue. For cervical cancer, about two to about five fractions may be used with a total dose of about 30 Gy to about 45 Gy to the target tissue. This fractional application takes advantage of cell recovery differences between normal and proliferative tissue, e.g., cancerous tissue, because normal tissue tends to recover between fractions while proliferative tissue tends not to recover, or to recover at a slower rate.

Treatment planning (dose planning) may occur prior to the initiation of radiation therapy to determine a prescribed dose to be delivered to a volume of the target tissue. In some instances, the prescribed dose may specify a minimum dose to be delivered to a preferred depth outside the treatment cavity (the prescription depth). Other two-dimensional dose prescription regimes may be used as well, e.g., when delivering radiation therapy to the pelvic area. The dose planning process may assess distances from cavity surfaces to skin surfaces or to other radiation sensitive structures (e.g., the rectum, bladder, small bowel) and may use these distances in combination with the prescribed prescription depth to determine a dose profile and a dose cloud shape. In this manner, the radiation therapy that is delivered to the target tissue in a patient may be configured to provide a predetermined dose shape. The dose cloud may be of any suitable shape. For example, the dose cloud shape may be symmetric with respect to the central axis of the applicator, or asymmetric with respect to the central axis of the applicator.

The present treatment planning system and method, which may also be applicable to devices other than the above-described tandem 12, involves the generation of a visual graph (in real-time) on a computer screen. The graph is known as the dose-volume histogram, and is a graph Volume (percentage or actual) versus Dose, for treatment or dose planning. The system may include the computer 32 or the handheld mobile device 34 and the associated processors and memory having processor-executable instructions stored thereon for generation of an image of the histogram and the tandem 12 on the computer screen, as described further hereinbelow. In other embodiments, the system may be cloud-based, and the screen may be generated on a local monitor or screen from a server computer running suitable software over the Internet with suitable encryption to protect patient privacy. One of ordinary skill in the art may select suitable computers and software configurations for the treatment planning system of performing the method of the present disclosure, as desired.

Figure 5:
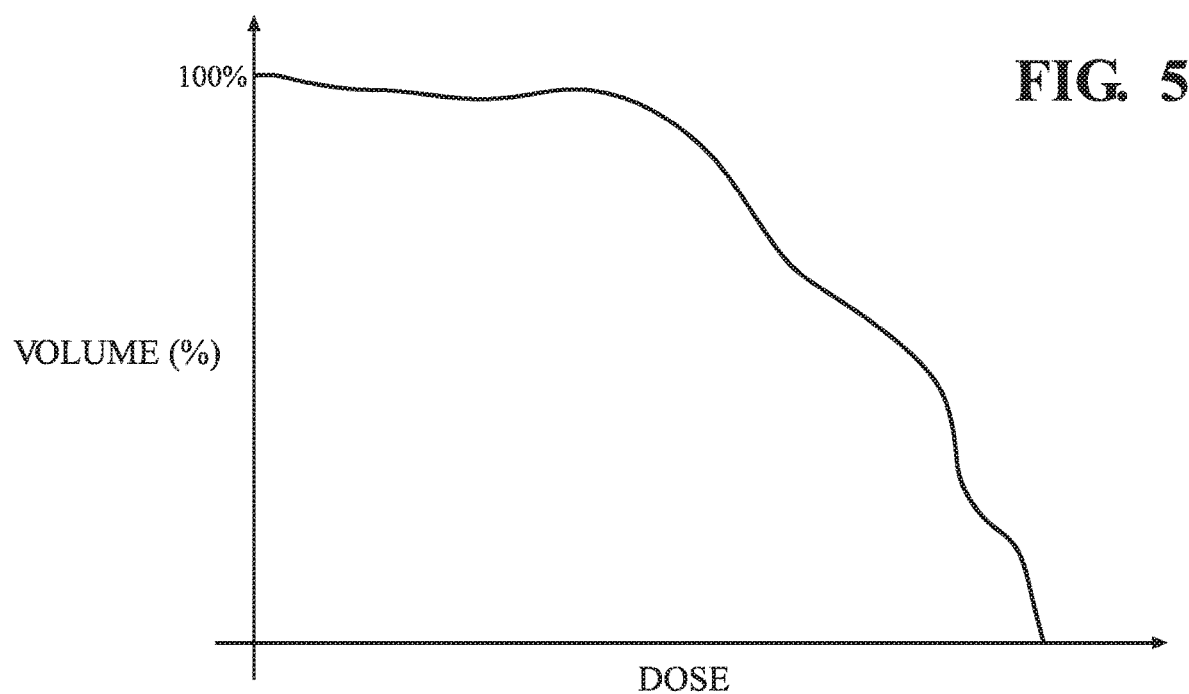
FIG. 5 is a graph with an illustrative curve representing a dose-volume histogram resulting from a set of the dwell positions and dwell times associated with a brachytherapy treatment according to the present disclosure.

In one example, as shown in the illustrative histogram of FIG. 5, each organ (cancer or not) may be represented by a curve. The shape of each curve is determined by locations known as "dwell positions," where the radioactive source stops inside the tandem 12, and also how long the radioactive source stops there, which is known as "dwell times." FIG. 5 shows one such curve resulting from a set of dwell positions and dwell times.

Figure 6:
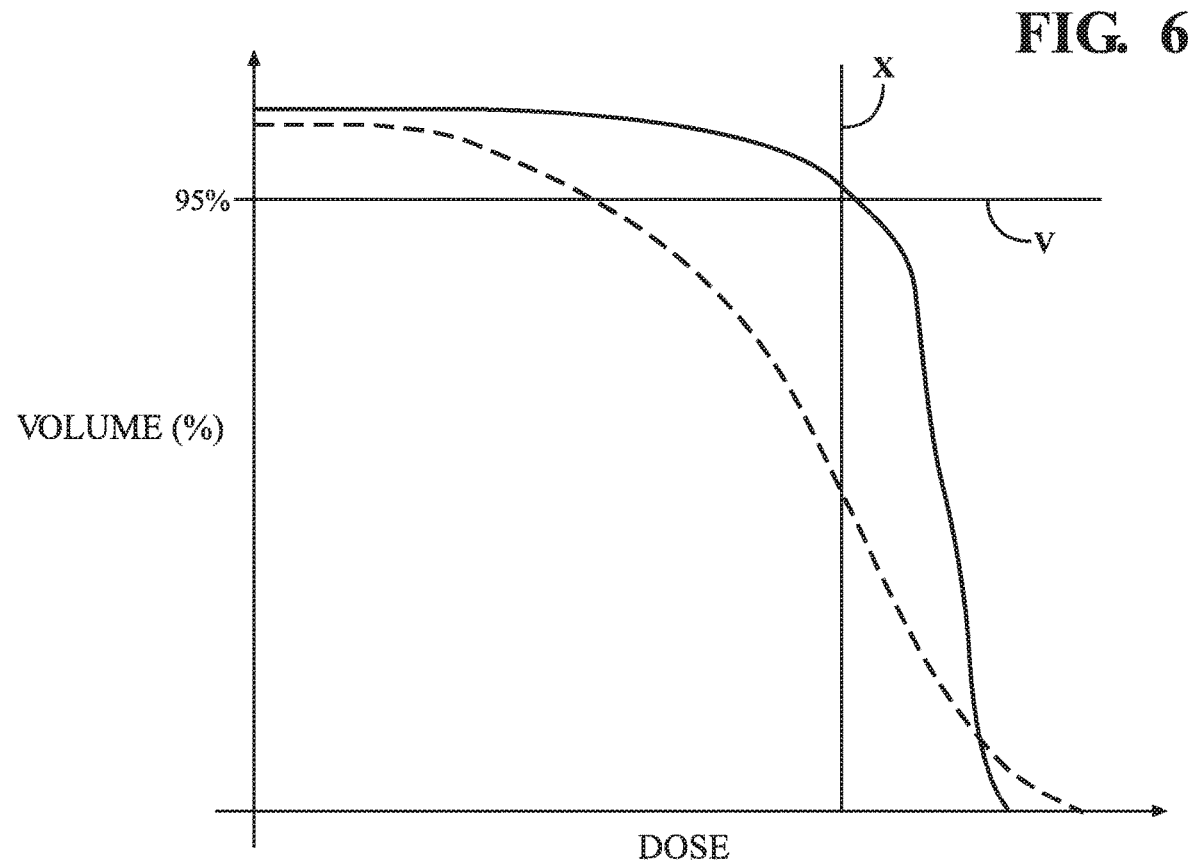
FIG. 6 is a graph illustrating a dose-volume histogram with an exemplary solid line curve resulting from a set of dwell positions and dwell times that satisfy a prescription, and an exemplary broken line curve resulting from a set of dwell positions and dwell times that do not satisfy the prescription.

In accordance with the present system and method, cancer treatment may be prescribed using such histograms. In one example, at least 95% of the cancerous volume must receive at least X amount of radiation dose. In the present system and method, the prescription becomes two lines on the dose-volume histogram, for example, as shown in FIG. 6. A curve for the cancerous volume resulting from a set of dwell positions and dwell times must intersect line X above line V in order to satisfy the prescription. FIG. 6 shows the set of dwell positions and times resulting in the solid line curve to satisfy the prescription. Those dwell positions and times resulting in the broken line curve do not satisfy the prescription.

It should also be understood that the cancer prescription is not easy to satisfy normally because of dose constraints on normal organs. A constraint typically reads as follows:

No more than 5% (example) of the normal organ volume A can receive a dose higher than $Y_A$, and No more than 10% (example) of the normal organ volume B can receive a dose higher than $Y_B$, etc.

Figure 7:
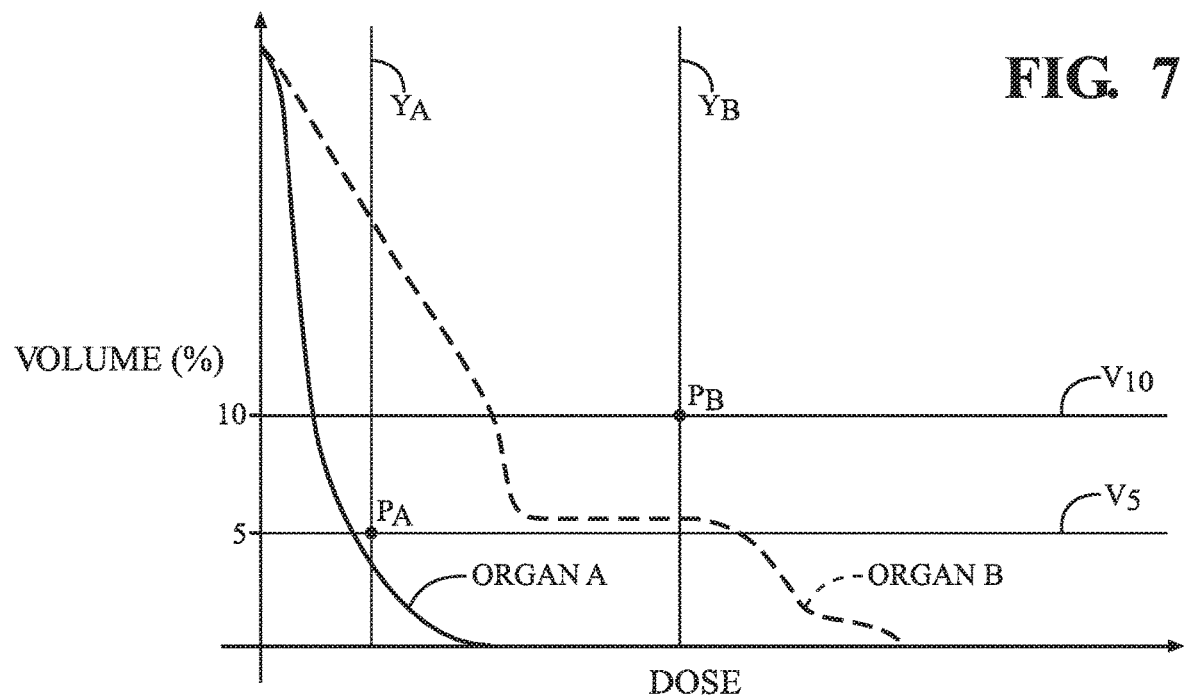
FIG. 7 is a graph illustrating a dose-volume histogram with a solid and broken line curves resulting from sets of dwell positions and dwell times that satisfy normal tissue constraints according to the present disclosure.

In the present system and method, each of these constraints becomes a pair of lines (just as the prescription becomes a pair of lines, i.e., line X and line V) on the dose-volume histogram. A shown in FIG. 7, a curve for a normal organ A results from a set of dwell positions and times must intersect the line $Y_A$ below the point $P_A$, etc. FIG. 7 shows the dose volume histograms as a solid line curve for organ A, and a broken line curve for organ B, resulting from a set of dwell positions and dwell times that satisfy normal tissue constraints.

Figure 8:
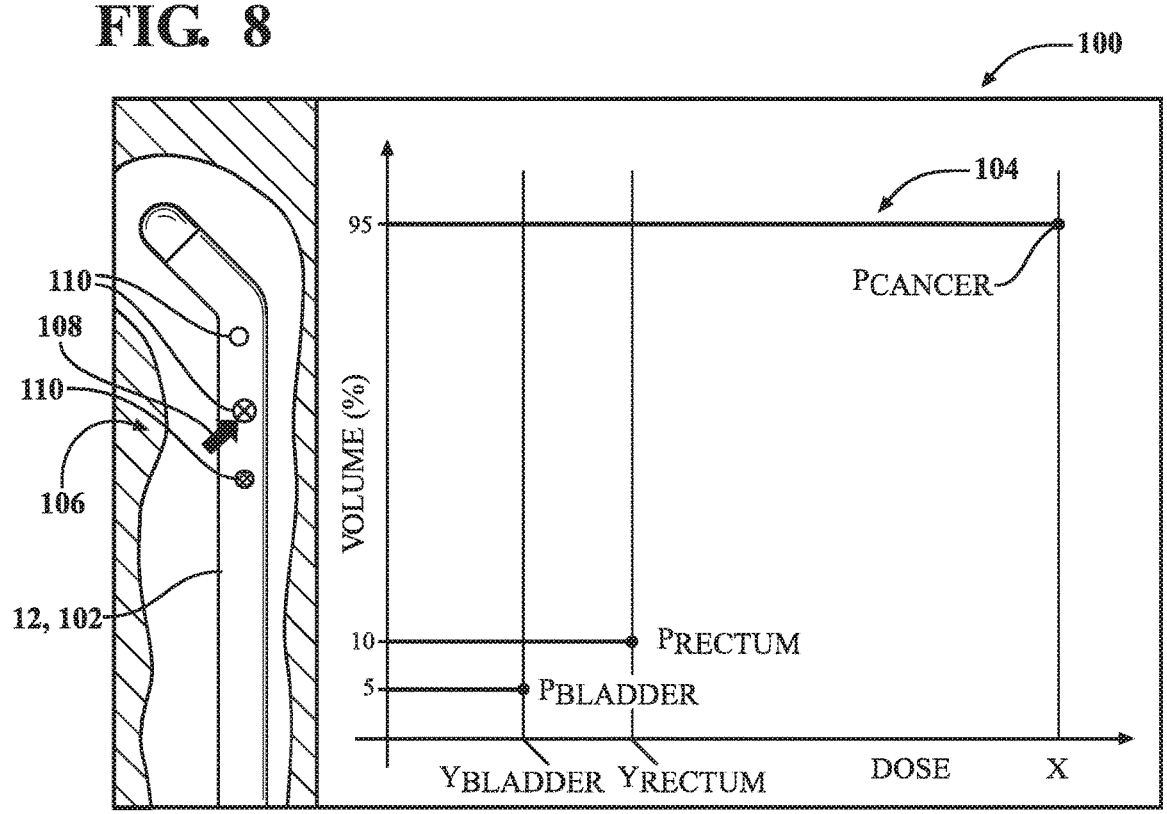
FIG. 8 is an illustrative screen generated on a computer or mobile device, and showing an instrument and dose volume histogram with target requirements for the cancer and the normal tissue dose constraints.

The present system and method puts these all together by generating an interactive image on a computer screen, for example, on the computer 32 or the handheld mobile device 34. On a computer screen 100, as shown in FIG. 8, a user sees a generated image 102 of the tandem 12 (or another suitable instrument with which the treatment planning system is being used) and a dose-volume histogram 104 with the dose constraints, e.g., $Y_{bladder}$, $Y_{rectum}$, and cancer prescription pairs of lines that are plotted and color coded. Optionally, as also shown in FIG. 8, the generated image of the tandem 12 may be superimposed on a composite image or model 106 generated from images of the body cavity of the patient 18 acquired by the camera system 26 in the tandem 12 during its positioning within the body cavity of the patient 18.

Figure 9:
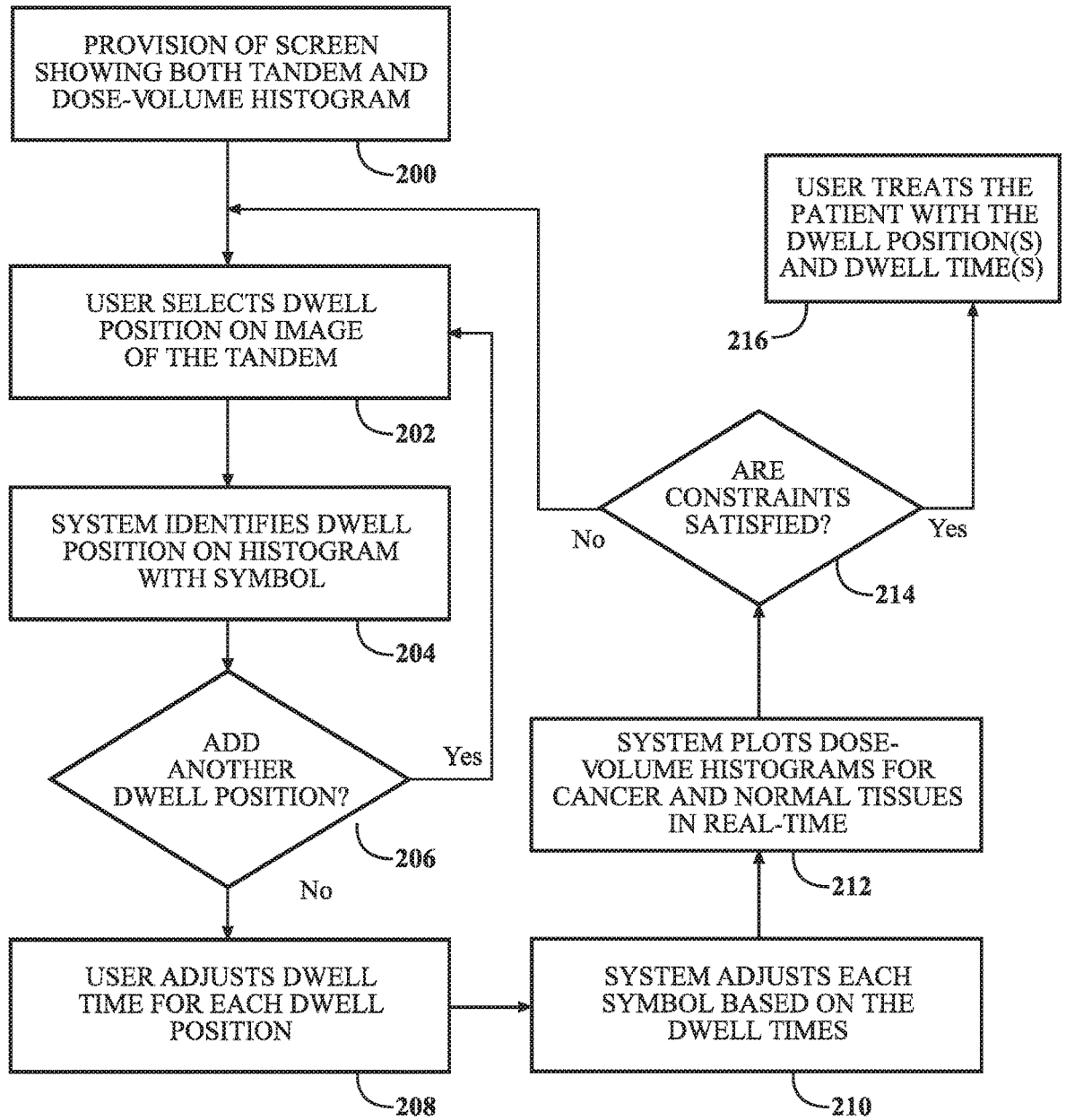
FIG. 9 is a flow diagram illustrating a method of using the tandem according to one embodiment of the present disclosure.
Figure 10:
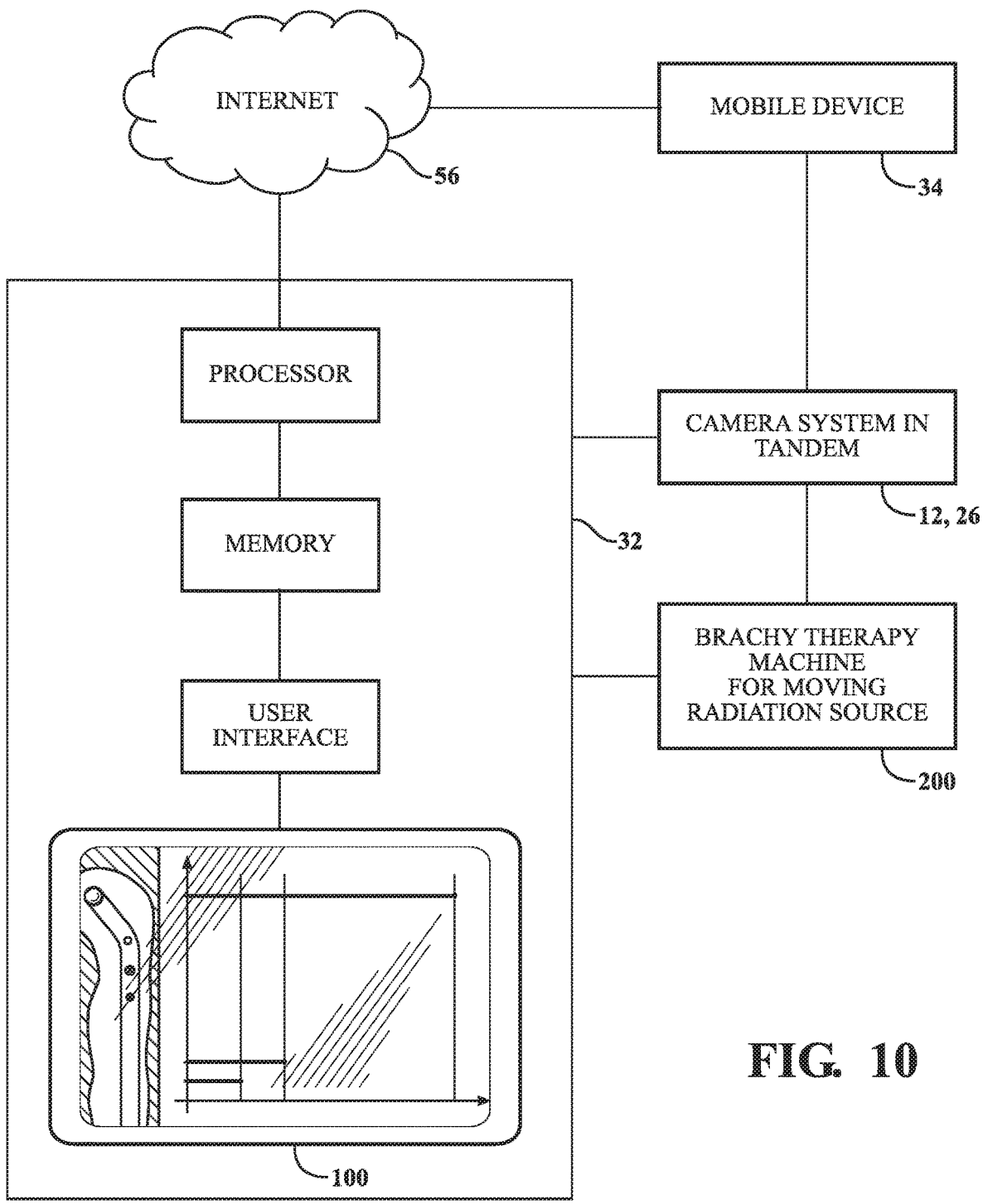
FIG. 10 is a diagram illustrating a treatment planning system according to one embodiment of the present disclosure.

The method and an exemplary system of the present disclosure are further shown in FIGS. 9 and 10. In a first step 200, and as described hereinabove, the treatment planning system (identified by reference number "32" in FIG. 10) provides the computer screen 100 showing both the image 102 of the tandem 12 and the dose-volume histogram 104. In step 202, the user then interacts with the image 102 of the tandem 12 on the screen (e.g., by clicking with a mouse arrow 108) to indicate a dwell position 110. In step 204, the system responds by making the dwell position 110 visible (e.g., as a white dot or circle on the screen). As many dwell positions 110 as desired can be initiated this way, as shown in step 206. One of ordinary skill in the art may also select other suitable means for identifying the dwell positions 110, within the scope of the present disclosure.

It should be appreciated that all initial dwell times may be assigned a value of zero (0) upon creation of the dwell positions 110 by the user. The dwell times may also be signified on the generated image 104 of the computer screen 100 by the intensity of the color of the positional dot or circle identifying the dwell positions 110, for example. One of ordinary skill in the art may also select other means for identifying the dwell times, as desired.

To increase the dwell time at a particular dwell position 110, in step 208 the user clicks and may hold down the mouse button 108 (left or right), or may use other means to increase the dwell time. The system responds in step 210 by making the initially white dot (or circle) colored, with an intensity corresponding to dwell time. To decrease the dwell time, the user may hold down the mouse button 108 (left or right) by clicking and holding (or by other means), with the system responding by lowering the intensity of the color for that dwell position 110. Other suitable means for permitting the user to decrease or increase the dwell time may also be used within the scope of the instant disclosure.

As the user performs these maneuvers, by adjusting the dwell position 110 and dwell time, the system in step 212 plots in real-time the various curves on the dose-volume histogram (as described hereinabove), and the user receives real-time feedback whether the current maneuver is satisfying the prescription and the constraints or not. It should be appreciated that this feedback in the form of the generated curves may be easily provided to the user simply by watching where all the curves are intersecting their respective vertical lines on the computer screen 100.

It should also be appreciated that the system-generated pairs of lines shown in FIG. 9 are not the only way to illustrate prescriptions and constrains on the generated image of the computer screen, since only the points $P_A$, $P_B$, $P_{cancer}$, $P_{bladder}$, etc. are important. So, although the generation of the lines provide a useful visual guide in practice, the lines are optional and can be omitted, if desired.

One of ordinary skill in the art will understand that the dwell positions are also not limited to a straight line (as is the case with the tandem 12) but can be three dimensional when the system is used for other devices, such as a ring.

Upon determining whether the constrains are satisfied in step 214, by the user visually reviewing the various curves on the dose-volume histogram, the user in step 216 may then treat the patient according to the dwell positions and dwell times, using a conventional brachytherapy machine 200 for advancing the radioactive material through the tandem 12.

Advantageously, the tandem applicator assembly 10, and the treatment planning system and method 200 described hereinabove, permit a visualization of the brachytherapy procedure, so as to avoid blind insertions and the risks of perforations during insertion of the tandem 12 into the body cavity of the patient. Furthermore, the treatment planning system and method 200 described hereinabove permits an efficient development of a treatment plan personalized to the patient 18 based on a real-time or near real-time imaging provided by the tandem applicator assembly 10 during the brachytherapy planning procedure.

While certain representative embodiments and details have been shown for purposes of illustrating the invention, it will be apparent to those skilled in the art that various changes may be made without departing from the scope of the disclosure, which is further described in the following appended claims.

What is claimed is:

1. A tandem applicator assembly for brachytherapy, comprising:
   a tandem having a tubular main body with a trail end and a lead end, a transparent cap affixed to the lead end;
   a camera system removably received by the tandem through the trail end of the tubular main body and disposed inside of the transparent cap, wherein the camera system includes at least one digital camera configured to acquire color images from a body cavity of a patient through the transparent cap and a main body having a camera portion with at least one lens, the at least one digital camera disposed inside of the main body beneath the at least one lens, the at least one digital camera configured to acquire the color images of the patient through both the at least one lens and the transparent cap; and
   an insertion and removal line coupled to the camera system and configured to selectively advance and retract the camera system through the tandem,
   wherein the main body of the camera system further has a transmitter in communication with a processor and a memory, the transmitter configured to generate a wireless signal with image data from the at least one camera, and
   wherein a portion of the transmitter abuts an inner surface of the tandem, and thereby causes the tubular main body of the tandem to be an antenna of the transmitter for transmission for the wireless signal.

2. The tandem applicator assembly of claim 1, wherein the transparent cap is a glass dome.

3. The tandem applicator assembly of claim 1, wherein the transparent cap is removably attached to the lead end of the tandem.

4. The tandem applicator assembly of claim 1, wherein the main body of the camera system further has a light configured to illuminate the patient, and wherein the light provides a directed beam via total internal reflection into the body cavity.

5. The tandem applicator assembly of claim 1, wherein the main body of the camera system further includes a processor and a memory in communication with the at least one camera, the processor configured to pre-process the color images of the patient to form a composite image, the memory configured to store both the color images and the composite image.

6. The tandem applicator assembly of claim 1, wherein the transmitter is in communication wirelessly with a handheld mobile device having a screen on which the color images or a composite image are generated.

7. A brachytherapy method, comprising the steps of:
   providing a tandem applicator assembly for brachytherapy, including a tandem having a tubular main body with a trail end and a lead end, a transparent cap affixed to the lead end, a camera system removably received by the tandem through the trail end of the tubular main body and disposed inside of the transparent cap, wherein the camera system includes at least one digital camera configured to acquire color images from a body cavity of a patient through the transparent cap and a main body having a camera portion with at least one lens, the at least one digital camera disposed inside of the main body beneath the at least one lens, the at least one digital camera configured to acquire the color images of the patient through both the at least one lens and the transparent cap, and an insertion and removal line coupled to the camera system and configured to selectively advance and retract the camera system through the tandem, wherein the main body of the camera system further has a transmitter in communication with a processor and a memory, the transmitter configured to generate a wireless signal with image data from the at least one camera, and wherein a portion of the transmitter abuts an inner surface of the tandem, and thereby causes the tubular main body of the tandem to be an antenna of the transmitter for transmission for the wireless signal;
   inserting the tandem applicator assembly into the body cavity of the patient while acquiring the color images in real-time or near real-time;
   reviewing the color images in order to confirm a desired positioning of the tandem applicator assembly within the body cavity of the patient;
   removing the camera system from the tandem; and
   inserting and moving a radioactive source through the trail end of the tubular main body to administer radiation to the patient according to a treatment plan.

8. The brachytherapy method of claim 7, wherein the processor is configured to pre-process the color images of the patient to form a composite image, and the memory is configured to store both the color images and the composite image.

9. The brachytherapy method of claim 7, wherein the camera system is in communication with a treatment planning system.

10. The brachytherapy method of claim 9, wherein the treatment planning system includes a computer with a processor and a memory defined by a non-transitory, tangible computer readable storage medium, the memory having processor-readable instructions embodied thereon and configured to generate an image on a computer screen of the tandem and an editable dose-volume histogram associated with the treatment plan.

11. The brachytherapy method of claim 10, wherein a user is permitted, by a user interface of the computer of the treatment planning system, to add at least one dwell position to the image of the tandem, and to adjust at least one dwell time associated with the at least one dwell position.

12. The brachytherapy method of claim 11, wherein the at least one dwell position is identified by a symbol generated by the treatment planning system on the dose-volume histogram, and the symbol changing in at least one of shape, color, and size depending on a magnitude of the at least one dwell time associated with the at least one dwell position and the symbol.

13. The brachytherapy method of claim 12, wherein the user interface includes a mouse, and the user is permitted to add the at least one dwell position by clicking a left or right button of the mouse, and to adjust the at least one dwell time by holding down the left or right button of the mouse to increase or decrease the at least one dwell time.

14. The brachytherapy method of claim 10, wherein a user is permitted, by a user interface of the computer of the treatment planning system, to view on a computer screen the color images of the body cavity of the patient, to facilitate a creation of the treatment plan.

* * * * *